(12) United States Patent
Bell

(10) Patent No.: US 7,361,339 B2
(45) Date of Patent: Apr. 22, 2008

(54) METHODS FOR REDUCING MORALITY ASSOCIATED WITH ACUTE MYOCARDIAL INFARCTION

(75) Inventor: Leonard Bell, Woodbridge, CT (US)

(73) Assignee: Alexion Pharmaceuticals, Inc., Cheshire, CT (US)

( * ) Notice: Subject to any disclaimer, the term of this patent is extended or adjusted under 35 U.S.C. 154(b) by 350 days.

(21) Appl. No.: 10/339,562

(22) Filed: Jan. 9, 2003

(65) Prior Publication Data

US 2004/0219147 A1  Nov. 4, 2004

(51) Int. Cl.
*A61K 39/395* (2006.01)

(52) U.S. Cl. ............... 424/130.1; 424/145.1; 424/158.1

(58) Field of Classification Search ............ None
See application file for complete search history.

(56) References Cited

U.S. PATENT DOCUMENTS

| | | | |
|---|---|---|---|
| 4,985,459 | A | 1/1991 | Sunshine et al. |
| 5,135,916 | A | 8/1992 | Sims et al. |
| 5,506,247 | A | 4/1996 | Sindelar et al. |
| 6,074,642 | A | 6/2000 | Wang et al. |
| 6,153,591 | A | 11/2000 | Cai et al. |
| 6,258,121 | B1 | 7/2001 | Yang et al. |
| 6,333,034 | B1 | 12/2001 | Gupta-Bansal et al. |
| 6,355,245 | B1 | 3/2002 | Evans et al. |
| 6,358,556 | B1 | 3/2002 | Ding et al. |
| 2002/0094332 | A1 | 7/2002 | Bell |
| 2003/0049260 | A1 | 3/2003 | Bell |
| 2004/0219147 | A1 | 11/2004 | Bell |

FOREIGN PATENT DOCUMENTS

| WO | WO-95/25540 | 9/1995 |
|---|---|---|
| WO | WO-01/70266 | 9/2001 |

OTHER PUBLICATIONS

"Apoptosis in Neuronal Development and Transplantation: Role of Caspases and Trophic Factors," Exp. Neurol. 156:1-156 (1999).
Buerke et al., J. Immunol. 167:5375-5380 (2001).
de Zwaan et al., Eur. Heart J. 23:1670-1677 (2002).
Faxon et al., JACC, vol. 40, pp. 1199-1204, 2002.
Fitch et al., Circulation 100:2499-2506 (1999).
Granger et al., Circulation 108:1184-1190 (2003).
Gray et al., Circulation 66:1185-1189 (1982).
Mollnes et al., Scand. J. Immunol. 28:307-312 (1988).
Pharmaceutical Journal, 269:803 Dec. 7, 2002.
Thomas et al., Molecular Immunology 33:1389-1401 (1996).
Vakeva et al., Circulation 22:2259-67 (1988).
Wurzner et al., Complement Inflamm. 8:328-340 (1991).
Babapulle and Eisenberg, 2002, Coated Stents for the Prevention of Restenosis: Part II, Circulation 106(22):2859-2866.
Babapulle and Eisenberg, 2002, Coated Stents for the Prevention of Restenosis: Part I, Circulation 106(21):2734-2740.
Beohar et al., 2001, Inhibition of Balloon Injury Mediated Apoptosis With Local Delivery of a Caspase Inhibitor, J. Ameican College of Cardiology, 37(2):44A.
de Zwaan et al., 2002, Continuous 48-h C1-inhibitor treatment, following repefusion therapy, in patients with acute myocardial infarction, Eur. Heart Jorunal, 23:1670-1677.
Funada et al., 1999, Effects of combined therapy with isosorbide dinitrate and nicorandil both on the coagulation system and on platelet activity after coronary stenting, Database accession No. EMB-1999131422.
Research and Development, Antibody fragment reduces mortality, Pharm. Journal, Dec. 7, 2002, p. 803.
Younossi et al., 1997, Effect of Combined Anticoagulation and Low-Dose Aspirin Treatment on Upper Gastrointestinal Bleeding, Digestive Diseases and Sci. 42(1):79-82.

*Primary Examiner*—Christina Chan
*Assistant Examiner*—F. Pierre VanderVegt
(74) *Attorney, Agent, or Firm*—Ropes & Gray LLP

(57) ABSTRACT

Methods of reducing mortality in myocardial infarction patients receiving a stent in connection with percutaneous transluminal coronary angioplasty include administering an anti-inflammatory compound to the patient. In one embodiment, the anti-inflammatory compound is an antibody to a complement component.

23 Claims, No Drawings

METHODS FOR REDUCING MORALITY ASSOCIATED WITH ACUTE MYOCARDIAL INFARCTION

BACKGROUND

1. Technical Field

This disclosure relates to methods for reducing mortality in myocardial infarction patients. More specifically, this disclosure relates to the administration of an anti-inflammatory compound to myocardial infarction patients receiving a stent in connection with percutaneous transluminal coronary angioplasty.

2. Background of Related Art

Approximately 1,000,000 patients in the U.S. survive an acute myocardial infarction (MI) each year. In an acute MI, severe restriction of blood flow in the coronary conduit vessels leads to reduced oxygen delivery to the myocardium and a subsequent cascade of inflammatory reactions resulting in death (infarction) of myocardial tissue. Percutaneous transluminal coronary angioplasty (PTCA) is widely used as the primary treatment modality in many patients with coronary artery disease. PTCA can relieve myocardial ischemia in patients with coronary artery disease by reducing lumen obstruction and improving coronary flow. The use of this surgical procedure has grown rapidly, with over 500,000 PTCAs per year. Stenosis following PTCA remains a significant problem, with from 25% to 35% of the patients developing restenosis within 1 to 3 months. Restenosis results in significant morbidity and mortality and frequently necessitates further interventions such as repeat angioplasty or coronary bypass surgery.

Despite the advent of thrombolysis and percutaneous transluminal coronary angioplasty (PTCA) to restore blood flow in approximately 40-90% of treated acute MI patients, a further inflammatory reaction (termed "reperfusion injury") results in additional tissue damage after the successful restoration of blood flow to the previously ischemic myocardium. Myocardial infarction is still associated with a high mortality/morbidity. In addition to severe long-term clinical morbidities and mortality related to post-MI pump dysfunction, short-term mortality ranges from 5% to 30%, depending in part upon successful acute revascularization, clinical presentation, co-morbidities, and site of infarction. Therefore, additional therapeutic modalities that impact myocardial tissue damage in acute MI could significantly reduce patient morbidity and mortality.

Reperfusion therapy has been shown to be beneficial in reducing mortality following acute MI. Earlier and more complete reperfusion is related to improved survival. There is, however, evidenced that reperfusion itself may result in deleterious adverse effects, including myocyte necrosis, microvascular injury, myocardial stunning, and arrhythmias. There is some debate about the clinical relevance of these phenomena. The actual mechanism of reperfusion injury has not been fully characterized but is believed to be caused by several different mechanisms: the formation of oxygen-free radicals, changes in intracellular calcium homeostasis, recruitment of neutrophils, complement activation, disturbed endothelial function, impaired cellular energetics, and alterations to the extracellular collagen matrix.

The pathogenesis of myocardial ischemic/reperfusion (MI/R) injury was investigated in a rat model of MI/R injury, during which it was noted that anti-C5 therapy significantly inhibited cell apoptosis, necrosis, and polymorphonuclear (PMN) leukocyte infiltration despite C3 deposition. This work suggests that the terminal components C5a and C5b-9 are key mediators of tissue injury in MI/R injury. The results from this experiment demonstrate the potential efficacy of anti-C5 mAb therapy in reducing both the initial tissue damage as well as the reperfusion inflammatory reaction in patients with acute MI.

Complement can be activated through either the classical or alternative pathways. These merge to a final common pathway in which C5 plays a critical role and is cleaved to form C5a and C5b. C5a is the most potent anaphylatoxin known, and has potent pro-inflammatory properties. It induces changes in smooth muscle and vascular tone, as well as increasing vascular permeability. It also activates both neutrophils and endothelial cells. C5 cleavage also leads to the formation of C5b-9 or the membrane attack complex, which causes vesiculation of platelets and endothelial cells, formation of pro-thrombotic microparticles, and activation of leukocytes and endothelial cells.

h5G1.1-scFv is an anti-C5 monoclonal antibody (mAb) that is designed to prevent the cleavage of C5 into its pro-inflammatory by-products. (See, U.S. Pat. No. 6,355,245, the disclosure of which is incorporated herein by this reference.) At the same time, blockade of the complement system at C5 preserves the patient's ability to generate C3b, which is critical for opsonization of pathogenic microorganisms and immune complex clearance.

Monoclonal antibodies directed against rat C5 were prepared and tested in vivo on rats to evaluate the role of complement in MI/R-induced apoptosis and necrosis. See, Vakeva, et al., Circulation, (22):2259-67 (1998). When administered to rats in which myocardial ischemia was induced, the anti-rat C5 mAbs reduced MI/R-induced necrosis and PMN infiltration in the rat and attenuated MI/R-induced apoptosis in the rat.

Unfortunately, most agents that have been shown to reduce infarct size in animal models of reperfusion have been disappointing when studied in large patient populations. For example, antibodies to either one or all of the four isoforms of the CD11/CD18 integrin receptor have been shown to reduce infarct size in animal studies. However in human studies, one such antibody (Hu23F2G) failed to show any effect on infarct size. (See, Faxon et al., JACC, vol. 40, pages 1199-1204, 2002.) Faxon et al. also failed to recognize any significant reduction in mortality or any relationship between mortality, antibody dosage and the use of stents during PTCA.

Thus, there is an unmet need for agents that may lessen reperfusion injury and improve mortality in the face of acute myocardial infarction. The 3 to 6 month mortality following acute MI in the 1990s is still approximately 5% to 10%, depending on the patient population studied. In addition, a substantial number of patients suffer in-hospital heart failure and subsequent re-hospitalization for congestive heart failure (CHF) in the months to years following an index MI. New adjunctive therapies to reperfusion therapy are needed to further attenuate the reperfusion injury phenomenon and improve outcomes from acute MI.

While stents have been useful in treating coronary disease, their use can cause various effects which are undesirable. For example, stents have been found to cause trauma to the walls of blood vessels resulting in medial injury that will further evolve over time. Also, stents can cause further intravascular damage and potentially distort blood flow with the creation of separate lumens within the intravascular space. Damage from stents in the vessel wall and to the flowing blood constituents can also generate debris that is carried downstream either acutely or over time. These effects, while present to some degree in different types of reperfusion therapy, are particularly prominent when reperfusion therapy is accompanied by placement of a stent.

It would be advantageous to decrease mortality in myocardial infarction patients receiving a stent in connection with percutaneous transluminal coronary angioplasty.

SUMMARY

A method of reducing mortality in myocardial infarction patients receiving a stent in connection with percutaneous transluminal coronary angioplasty has now surprisingly been found. This method includes administering an anti-inflammatory compound to a myocardial infarction patient receiving a stent in connection with percutaneous transluminal coronary angioplasty. In one embodiment, a dose of the anti-inflammatory compound is administered prior to the angioplasty and then the anti-inflammatory compound is administered over a period of time after the angioplasty. The anti-inflammatory compound can be, for example, an NSAID, an antiapotopic compound, a molecule that binds to or otherwise blocks the generation and/or activity of integrins or adhesion molecules, or a compound which binds to or otherwise blocks the generation and/or activity of complement components (e.g., an antibody to a complement component).

DETAILED DESCRIPTION OF PREFERRED EMBODIMENTS

Using the methods in accordance with this disclosure, mortality in myocardial infarction patients receiving a stent in connection with percutaneous transluminal coronary angioplasty is reduced by administering an anti-inflammatory compound to a myocardial infarction patient receiving a stent in connection with percutaneous transluminal coronary angioplasty. The present methods can reduce mortality in such patients by up to about 70%.

Anti-inflammatory compounds which can be used in the methods described herein include non-steroidal anti-inflammatory drugs (NSAIDS). The NSAIDS can be selected from the following categories: propionic acid derivatives; acetic acid derivatives; fenamic acid derivatives; biphenylcarboxylic acid derivatives; and oxicams. All of these NSAIDS are fully described in the U.S. Pat. No. 4,985,459 to Sunshine et al., issued Jan. 15, 1991, incorporated by reference herein. Most preferred are the propionic NSAIDS including, but not limited to aspirin, acetaminophen, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid. Another useful class of anti-inflammatory compounds include inhibitors of cyclooxygenase-1 (COX-1) and inhibitors of cyclooxygenase-2 (COX-2). Also useful are the steroidal anti-inflammatory drugs including hydrocortisone and the like. Particularly useful are anti-inflammatory compounds which reduce neutrophil activation or monocyte activation by greater than about 30% or which reduce apoptosis by about 30%.

Useful agents that reduce apoptosis include caspase inhibitors. Suitable caspase inhibitors include any compound or composition having inhibitory activity to one or more caspase enzymes reactive with cardiac cells. Such caspase inhibitors include, but are not limited to, z-VAD-DCB (an irreversible ICE/caspase-1 inhibitor), z-DEVD-fmk (a rather specific inhibitor of caspase-3), viral caspase inhibitor gene p35 and broad spectrum caspase inhibitor benzyloxycarbonyl-Val-Ala-Asp-fluoromethylketone (z-VAD-fmk) (inhibiting caspase-3 or caspase like proteases), benzoylcarbonyl-Asp-CH2OC(O)-2,6-dichlorobenzene (Z-Asp-DCB), caspase 3/7-selective inhibitors such as, for example, (S)-(+)-5(1-(2-methoxymethylpyrrolidinyl) sulfonyl)isatin ("MMPSI"), caspase 8 inhibitors such as, for example, Z-IETD-fmk; caspase 9 inhibitors such as, for example, benzoxycarbonyl-Leu-Glu-OMe-His-Asp(OMe)-fluoromethylketone (z-LEHD-fmk); caspase 3 inhibitors such as, for example, acetyl-Asp-Glu-Val-Asp-cmk (Ac-DEVD-cmk), and acetyl-DEVD-CHO; Bocaspartyl(OMe)-fluoromethylketone (BAF or BocD-fmk) (inhibitor of caspase-1 and caspase-3), and caspase-1-specific inhibitors, e.g., Ac-Try-Val-Ala-Asp-chloromethylketone (Y-VAD-cmk), YVAD-aldehyde, YVAD, DEVD-aldehyde, DEVD, Ac-Try-Val-Ala-Asp-aldehyde, crmA (a cytokineresponse modifier gene and a viral caspase inhibitor), Ac-YVAD-cmk (an inhibitor of caspase 1), acetyl-Tyr-Val-Ala-Asp-chloromethylketone (Ac-YVAD-fmk), CPP (an inhibitor of caspases 1 and 3), z-DEVD-fmk (an inhibitor of caspase 3) and angiotensin-converting enzyme (ACE) inhibitors such as, for example, the drug enalaprilat. Other known caspase inhibitors can be used such as those disclosed in U.S. Pat. No. 6,153,591 and "Apoptosis in Neuronal Development and Transplantation: Role of Caspases and Trophic Factors", Exp. Neurol. 156: 1-156(1999), the contents of which are incorporated herein by reference. It should be understood that combinations of caspase inhibitors can be employed in the compositions and methods described herein. Preferably, the caspase inhibitor is not specific to one caspase. Particularly useful caspase inhibitors are bocaspartyl(o-methyl)-flouromethylketone (BAF) and Ac-YVAD-cmk. Other compounds having antiapoptopic effect that are useful herein include the drug nicorandil, nitric oxide (NO), insulin-like growth factor I (IGF-I) and phosphatidylinnositol 3 kinase (P13 kinase)

Other anti-inflammatory compounds include molecules that bind to or otherwise block the generation and/or activity of integrins or adhesion molecules. Such molecules include compounds that interfere with or mediate leukocyte recruitment to sites of inflammation through adhesion to leukocyte surface ligands, such as, for example, LFA-1 (CD11a/CD18 complex) on neutrophils and other leukocytes and Mac-1 (CD11b/CD18) on phagocytes. Accordingly, among the suitable anti-inflammatory compounds for use herein include anti-integrin antibodies and anti-adhesion molecule antibodies.

Preferred anti-inflammatory compounds are compounds which bind to or otherwise block the generation and/or activity of complement components. A specific class of such compounds which are particularly useful are antibodies specific to a human complement component.

The complement system acts in conjunction with other immunological systems of the body to defend against intrusion of cellular and viral pathogens. There are at least 25 complement proteins, which are found as a complex collection of plasma proteins and membrane cofactors. The plasma proteins make up about 10% of the globulins in vertebrate serum. Complement components achieve their immune defensive functions by interacting in a series of intricate but precise enzymatic cleavage and membrane binding events. The resulting complement cascade leads to the production of products with opsonic, immunoregulatory, and lytic functions. A concise summary of the biologic activities associated with complement activation is provided, for example, in The Merck Manual, 16$^{th}$ Edition.

The complement cascade progresses via the classical pathway or the alternative pathway. These pathways share many components, and while they differ in their initial steps, they converge and share the same "terminal complement" components (C5 through C9) responsible for the activation and destruction of target cells. The classical complement pathway is typically initiated by antibody recognition of and binding to an antigenic site on a target cell. The alternative pathway is usually antibody independent, and can be initiated by certain molecules on pathogen surfaces. Additionally, the lectin pathway is typically initiated with binding of mannose-binding lectin (MBL) to high mannose substrates. These pathways converge at the point where complement component C3 is cleaved by an active protease (which is different in each pathway) to yield C3a and C3b. Other pathways activating complement attack can act later in the sequence of events leading to various aspects of complement function.

C3a is an anaphylatoxin (see discussion below). C3b binds to bacterial and other cells, as well as to certain viruses and immune complexes, and tags them for removal from the circulation. (C3b in this role is known as opsonin.) The opsonic function of C3b is generally considered to be the most important anti-infective action of the complement system. Patients with genetic lesions that block C3b function are prone to infection by a broad variety of pathogenic organisms, while patients with lesions later in the complement cascade sequence, i.e., patients with lesions that block C5 functions, are found to be more prone only to Neisseria infection, and then only somewhat more prone (Fearon, in Intensive Review of Internal Medicine, $2^{nd}$ Ed. Fanta and Minaker, eds. Brigham and Women's and Beth Israel Hospitals, 1983).

C3b also forms a complex with other components unique to each pathway to form classical or alternative C5 convertase, which cleaves C5 into C5a and C5b. C3 is thus regarded as the central protein in the complement reaction sequence since it is essential to both the alternative and classical pathways (Wurzner, et al., Complement Inflamm. 8:328-340, 1991). This property of C3b is regulated by the serum protease Factor I, which acts on C3b to produce iC3b. While still functional as opsonin, iC3b cannot form an active C5 convertase.

C5a is another anaphylatoxin (see discussion below). C5b combines with C6, C7, and C8 to form the C5b-8 complex at the surface of the target cell. Upon binding of several C9 molecules, the membrane attack complex (MAC, C5b-9, terminal complement complex—TCC) is formed. When sufficient numbers of MACs insert into target cell membranes the openings they create (MAC pores) mediate rapid osmotic lysis of the target cells. Lower, non-lytic concentrations of MACs can produce other effects. In particular, membrane insertion of small numbers of the C5b-9 complexes into endothelial cells and platelets can cause deleterious cell activation and apoptosis. In some cases activation may precede cell lysis.

As mentioned above, C3a and C5a are anaphylatoxins. These activated complement components can trigger mast cell degranulation, which releases histamine and other mediators of inflammation, resulting in smooth muscle contraction, increased vascular permeability, leukocyte activation, and other inflammatory phenomena including cellular proliferation resulting in hypercellularity. C5a also functions as a chemotactic peptide that serves to attract pro-inflammatory granulocytes to the site of complement activation.

Any compounds which bind to or otherwise block the generation and/or activity of any of the human complement components, such as, for example, antibodies specific to a human complement component are useful herein. Some compounds include 1) antibodies directed against complement components C-1, C-2, C-3, C-4, C-5, C-5a, C-6, C-7, C-8, C-9, Factor D, Factor B, Factor P, MBL, MASP-1, AND MASP-2 and 2) naturally occurring, modified, or soluble forms of complement inhibitory compounds such as CR1, LEX-CR1, MCP, DAF, CD59, Factor H, cobra venom factor, FUT-175, complestatin, and K76 COOH. Suitable compounds for use herein are antibodies that reduce, directly or indirectly, the conversion of complement component C5 into complement components C5a and C5b. One class of useful antibodies are those having at least one antibody-antigen binding site and exhibiting specific binding to human complement component C5, wherein the specific binding is targeted to the alpha chain of human complement component C5. Such an antibody 1) inhibits complement activation in a human body fluid; 2) inhibits the binding of purified human complement component C5 to either human complement component C3 or human complement component C4; and 3) does not specifically bind to the human complement activation product for C5a. Particularly useful complement inhibitors are compounds which reduce the generation of C5a and/or C5b-9 by greater than about 30%. A particularly useful anti-C5 antibody is h5G1.1-scFv. Methods for the preparation of h5G1.1-scFv are described in U.S. patent application Ser. No. 08/487,283 filed Jun. 7, 1995 now U.S. Pat. No. 6,355,245 and "Inhibition of Complement Activity by Humanized Anti-C5 Antibody and Single Chain Fv", Thomas et al., *Molecular Immunology*, Vol. 33, No. 17/18, pages 1389-1401,1996, the disclosures of which are incorporated herein in their entirety by this reference.

The route of administration of the anti-inflammatory compound is in accord with known methods, e.g., injection or infusion by intravenous, intraperitoneal, intracerebral, intramuscular, subcutaneous, intraocular, intraarterial, intrathecal, inhalation or intralesional routes, topical or by sustained release systems as noted below. The anti-inflammatory compound is preferably administered continuously by infusion or by bolus injection. One may administer the anti-inflammatory compounds in a local or systemic manner. One may administer the anti-inflammatory compound coated on a surface of the stent. Techniques for preparing coated stents are within the purview of one skilled in the art. See, for example, U.S. Pat. Nos. 6,358,556 and 6,258,121, the disclosures of which are incorporated herein by this reference.

In particularly useful embodiments, a first dose of the anti-inflammatory compound is administered prior to the percutaneous transluminal coronary angioplasty, followed by a steady infusion of a second dose of the anti-inflammatory compound over a period of time. The infusion of the second dose of the anti-inflammatory compound preferably begins no later than 4 hours after the first dose. The infusion of the second dose of the anti-inflammatory compound should be administered over a period of at least 4 hours, preferably 8 to 24 hours, more preferably, over a period of 12 to 20 hours. However, it should be understood that other dosage regimes may also be useful.

The anti-inflammatory compound may be prepared in a mixture with a pharmaceutically acceptable carrier. Techniques for formulation and administration of the compounds of the instant application may be found in "Remington's Pharmaceutical Sciences," Mack Publishing Co., Easton, Pa., latest edition. This therapeutic composition can be administered intravenously or through the nose or lung, preferably as a liquid or powder aerosol (lyophilized). The composition may also be administered parenterally or subcutaneously as desired. When administered systematically, the therapeutic composition should be sterile, pyrogen-free and in a parenterally acceptable solution having due regard for pH, isotonicity, and stability. These conditions are known to those skilled in the art.

Briefly, dosage formulations of the anti-inflammatory compound are prepared for storage or administration by mixing the compound having the desired degree of purity with physiologically acceptable carriers, excipients, or stabilizers. Such materials are non-toxic to the recipients at the dosages and concentrations employed, and may include buffers such as TRIS HCl, phosphate, citrate, acetate and other organic acid salts; antioxidants such as ascorbic acid; low molecular weight (less than about ten residues) peptides such as polyarginine, proteins, such as serum albumin, gelatin, or immunoglobulins; hydrophilic polymers such as polyvinylpyrrolidinone; amino acids such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium and/or nonionic surfactants such as TWEEN, PLURONICS or polyethyleneglycol. When used for in vivo administration, the anti-inflammatory formulation must be sterile and can be formulated according to conventional pharmaceutical practice.

The dosage of the anti-inflammatory compound employed will depend on a number of factrors, including, but not limited to the specific anti-inflammatory compound to be administered. Toxicity and therapeutic efficacy of the anti-inflammatory molecules described herein can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. The data obtained from these cell culture assays and animal studies can be used in formulating a range of dosage for use in human. The dosage of such molecules lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g., Fingl et al., 1975, in "The Pharmacological Basis of Therapeutics", Ch. 1 p.1). A typical daily dosage might range from about 0.001 mg/kg to abut 1000 mg/kg, more preferably about 0.01 mg to 100 mg/kg, more preferably about 0.050 to 20 mg/kg of the anti-inflammatory compound might be an initial candidate dosage for administration to the patient.

Techniques for performing percutaneous transluminal coronary angioplasty with the placement of a stent are with the purview of those skilled in the art.

The following non-limiting example is included to illustrate the present invention but is not intended to limit the scope thereof.

EXAMPLE 1

A Randomized, Double-Blind, Placebo-Controlled Study of Two Intravenous Dosing Regimens of h5G1.1-scFv in Patients with Acute Myocardial Infarction Undergoing Percutaneous Transluminal Coronary Angioplasty Reperfusion Therapy A multi-center, randomized, double blind, placebo-controlled study was conducted of the intravenous (IV) administration of h5G1.1-scFv in conjunction with PTCA reperfusion therapy within 6 hours of onset of symptoms of acute MI. Patients were divided into 3 treatment groups. The treatment regimen for each group was as follows:

| Patient Group | Bolus over 10 minutes | Reperfusion | Time to Infusion | Infusion over 20 hours |
|---|---|---|---|---|
| 1 (n = 281) | 2.0 mg/kg | PTCA | 4 hours | 1.0 mg/kg h5G1.1-scFv |
| 2 (n = 262) | 2.0 mg/kg | PTCA | 4 hours | Placebo |
| 3 (n = 271) | Placebo | PTCA | 4 hours | Placebo |

Patients were screened upon arrival to the emergency room. There was a 24-hour treatment period and a 6-month follow-up period. The 24-hour treatment period proceeded as follows: A bolus of h5G1.1-scFv or placebo (depending on the patient's group assignment) was infused intravenously over 10 minutes before PTCA. PTCA therapy began after the entire bolus dose of antibody or placebo was administered. Approximately 4 hours after the 10-minute administration of the bolus, an IV infusion began with h5G1.1-scFv or placebo, and continued for 20 hours, using a peristaltic pump (e.g., IMED) or similar device. The duration of treatment with study medication was, therefore, approximately 24 hours.

h5G1.1-scFv and matching placebo were supplied in glass vials and packaged as a solution for injection in 30 ml vials with a concentration of 2 mg/ml. This was a double-blind study. All personnel involved in the study were blinded to the dosing regimen for each patient.

Patients who presented within 6 house of onset of symptoms of an acute MI, as confirmed by ECG with 2 mm of ST segment elevation, participated in the study. Informed consent was obtained. Patients were stratified by location of MI (acute isolated inferior wall MI vs. acute non-inferior wall MI) and randomized by site to 1 of the 3 treatment groups described above. The Interactive Voice Activated Response System (IVRS) was used to track and record the MI profiles, and permitted the enrollment/randomization of patients with acute isolated inferior wall MI until the study-wide limit of such patients (approximately 200) had been reached. Once patients were randomized, baseline evaluations were performed followed by the administration of the anti-inflammatory compound or placebo. Patients received the bolus of study medication as soon as possible following the decision to perform PTCA therapy, determination of eligibility and signing of informed consent, but no later than 6 hours after the onset of symptoms. The entire bolus of study medication was given prior to the initiation of PTCA therapy, to protect against reperfusion injury. Patient observations were preformed through 72 hours, at discharge or day 6, day 14, day 30 and Day 90. At day 180, a 6-month follow-up telephone contact with the patient/representative took place. Thrombolysis In Myocardial Infarction (TIMI) flow was noted post PTCA procedure.

Safety monitoring included review of clinical laboratory test results, 12-lead EGG measurements, and frequency and severity of adverse events (AEs). Information regarding AEs was collected from the time informed consent is obtained through Day 90.

MI patients have elevated levels of C5b-9 upon arrival at the emergency room. Levels remain elevated through 24 hours, and have begun to decrease by 48 hours. Thus, the criterion for picking a dosing regimen for this study was based on the hypothesis that complete complement suppression be achieved for approximately 24 hours.

Pharmacodynamic data from previous studies indicate that a 2.0 or 4.0 mg/kg bolus of h5G1.1-scFv alone did not provide complete 24-hour complement inhibition. Similarly, 2 boluses of 2.0 mg/kg h5G1.1-scFV administered 6 hours apart did not provide complete 24 hours of inhibition. A dosing study in normal volunteers was conducted using a 2 mg/kg bolus of hG51.1-scFv followed either immediately for 24 hours or after a 4 hour delay for 20 hours with an infusion of placebo or infusion of 0.05, 0.10, 0.20 mg/kg/hr of hG51.1-scFv. Analysis of the pharmacodynamic profile revealed that serum complement hemolytic activity was almost completely blocked for at least 4 hours in subjects receiving the bolus of h5G1.1-scFv alone. Subjects who received the initial 2.0 mg/kg bolus plus the infusion at 0.05 or 0.1 mg/kg/hr completely blocked complement activity for at least 36 hours in most of the subjects. At 72 hours with the 0.05 mg/kg/hr infusion, there was essentially a complete return to baseline hemolytic complement activity in the majority of subjects (6 of 8). There was no significant difference in the overall incidence of adverse events between the placebo and active drug groups. Taken together, the pharmacodynamic and safety data suggest that a 2.0 mg/kg bolus followed by an infusion of 0.05 mg/kg/hr either immediately for 24 hours or for 20 hours after a four hour delay after bolus is well tolerated and sufficient to completely block damaging complement activity for a 24 hour period.

The study endpoint was reduction infarct size as determined by CK-MB AUC through 72 hours. A composite endpoint, composed of the clinical outcomes of death, new or worsening CHF, cardiogenic shock or stroke, and the individual components were secondary endpoints. Death was defined as all-caused mortality. The clinical outcome of congestive heart failure (CHF) was based on the physician's assessment and will include in hospital CHF occurring at least 24 hours after enrollment and re-hospitalization for CHF. Cardiogenic shock was defined as hypotension to less than 90 mmHg systolic blood pressure lasting for at least 1 hour, not responsive to fluid resuscitation alone, felt to be secondary to cardiac dysfunction, and associated with clinical signs of hypo perfusion. A stroke was defined as a new focal neurologic deficit classified according to the Stroke Patient Functional Status Scale (see below) as at least moderate or severe lasting until hospital discharge or 30 days (which ever comes first) or resulting in death and classified by a physician as a stroke.

Myocardial infarct size was determined by CK-MB AUC. Blood samples for CK MB were analyzed by a central laboratory. The extent of flow restoration/vessel patency following PTCA was noted by visual assessment of TIMI flow through the target vessel. The normal conventions for TIMI flow grades are as follows:

Grade 0—No perfusion; no antegrade flow beyond the point of occlusion

Grade 1—Penetration without perfusion; contrast material passes beyond the area of obstruction but fails to opacify the entire coronary bed distal to the obstruction for the duration of the cineangiographic filming sequence Grade 2—Partial perfusion; contrast material passes across the obstruction. However, the rate of entry of contrast material into the vessel distal to the obstruction or its rate of clearance from the distal bed (or both) is perceptibly slower than its flow into or clearance from comparable areas not perfused by the previously occluded vessel (e.g, opposite coronary artery or the coronary bed proximal to the obstruction)

Grade 3—Complete perfusion; antegrade flow into the bed distal to the obstruction occurs as promptly as antegrade flow into the bed proximal to the obstruction, and clearance of contrast material from the involved bed is as rapid as clearance from an uninvolved bed in the same vessel or the opposite artery.

To be eligible for enrollment into this study, the patient must have met all of the following criteria:

1. was at least 18 years of age.
2. had been experiencing continuous symptoms of ischemic (cardiac) discomfort for at least 20 minutes.
3. has an ECG showing one of the following:
    ST segment elevation$\geq 2$ mm in 2 contiguous precordial leads $V_1$-$V_6$, or
    ST segment elevation$\geq 2$ mm in leads I, AVL or
    St segment elevation$\geq 2$ mm in 2 contiguous leads II, III, AVF or
    New left bundle branch block.
4. presented to the emergency room, was eligible for PTCA reperfusion therapy, and would undergo PTCA within 6 hours of onset of chest pain.
5. provided informed consent (or legally authorized representative of the patient had provided informed consent).

A patient was ineligible for study entry if he/she met any of the following exclusion criteria:

1. had a known history of an abnormal hematological function, defined as Hgb<9.5 g/dl: WBC<$3\times10^3$/mm$^3$; neutrophils<1200/mm$^3$; platelets<100,000/mm$^3$.
2. had presence of or suspected active neisserial infection.
3. had a known or suspected hereditary complement deficiency.
4. participated in any other investigational drug study or been exposed to other investigational agent within 30 days.
5. was pregnant, breast feeding, or intended to conceive during the course of the study (including follow-up).

Patients were withdrawn from the study if the patient wished to withdraw or if an adverse event or intercurrent illness occurred that, in the investigator's opinion, necessitated withdrawal from the study after receiving any amount of study medication.

Laboratory analyses were performed as part of the safety evaluation. Upon discharge, patients and their families/caregivers were instructed to note the occurrence of any adverse events, and to note any changes in concomitant medications.

The study revealed that the administration of the anti-inflammatory compound, in this case h5G1.1-scFv, modestly reduced the incidence of largest infarcts. Although mortality appeared to be independent of infarct size in patients with TIMI 3 flow, h5G1.1-scFv reduced infarction size and reduced mortality in patients with suboptimal TIMI flow of 0 to 2. h5G1.1-scFv also reduced the incidence of cardiogenic shock and size of infarcts in patients with cardiogenic shock.

A statistical analysis of the 90 day mortality data collected showed a significant reduction in mortality with treatment in patients who also received stents (p=0.009 vs. placebo). The data are presented in the following table:

| Treatment | Stent Use? | Incidence (%) | 90 day mortality |
|---|---|---|---|
| Placebo | Yes | 90.4 | 6.1% |
| Bolus | Yes | 88.5 | 3.9% |
| Bolus + Infusion | Yes | 91.1 | 1.6%* |
| Placebo | No | 9.6 | 3.8% |
| Bolus | No | 11.5 | 6.7% |
| Bolus + Infusion | No | 8.9 | 4.0% |

*(p = 0.009 vs.placebo)

A substantial and dose-dependent 74% reduction in mortality was associated with the use of h5G1.1sc-Fv on top of concomitant stent therapy. There was no apparent reduction in mortality with anti-inflammatory compound administration in patients who did not also undergo concomitant stent placement.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended herein.

What is claimed is:

1. A method of treating acute myocardial infarction comprising:
    administering a mortality reducing amount of an anti-C5 antibody to a subject receiving a stent in connection with percutaneous transluminal coronary angioplasty.

2. The method as in claim 1 wherein the antibody is h5G1.1-scFv.

3. The method as in claim 1 wherein the antibody is an antibody that directly or indirectly reduces the conversion of complement component C5 into complement components C5a and C5b.

4. The method as in claim 3 wherein the antibody is an antibody comprising at least one antibody-antigen binding site, said antibody exhibiting specific binding to human complement component C5, said specific binding being targeted to the alpha chain of human complement component C5, wherein the antibody 1) inhibits complement activation in a human body fluid; 2) inhibits the binding of purified human complement component C5 to either human complement component C3 or human complement component C4; and 3) does not specifically bind to the human complement activation product for C5a.

5. A method of reducing mortality in a subject with acute myocardial infarction receiving a stent in connection with percutaneous transluminal coronary angioplasty comprising:
    administering to the subject a first dose of an anti-C5 antibody prior to performing the percutaneous transluminal coronary angioplasty; and
    subsequently administering a second dose of the anti-C5 antibody by intravenously infusing the subject over a period of at least 4 hours.

6. The method as in claim 5 wherein the second dose is administered no later than 4 hours after the first dose.

7. The method as in claim 5 wherein the second dose is administered over a period of 8 to 24 hours.

8. The method as in claim 5 wherein the second dose is administered over a period of 12 to 20 hours.

9. The method as in claim 5 wherein the antibody is h5G1.1-scFv.

10. The method as in claim 5 wherein the antibody is an antibody that directly or indirectly reduces the conversion of complement component C5 into complement components C5a and C5b.

11. The method as in claim 10 wherein the antibody is an antibody comprising at least one antibody-antigen binding site, said antibody exhibiting specific binding to human complement component C5, said specific binding being targeted to the alpha chain of human complement component C5, wherein the antibody 1) inhibits complement activation in a human body fluid; 2) inhibits the binding of purified human complement component C5 to either human complement component C3 or human complement component C4; and 3) does not specifically bind to the human complement activation product for C5a.

12. A method of reducing mortality in a subject with acute myocardial infarction receiving a stent in connection with percutaneous transluminal coronary angioplasty comprising administering an anti-C5 antibody to the subject.

13. The method as in claim 12 wherein the antibody is h5G1.1-scFv.

14. The method as in claim 12 wherein the antibody an antibody that directly or indirectly reduces the conversion of complement component C5 into complement components C5a and C5b.

15. The method as in claim 14 wherein the antibody is an antibody comprising at least one antibody-antigen binding site, said antibody exhibiting specific binding to human complement component C5, said specific binding being targeted to the alpha chain of human complement component C5, wherein the antibody 1) inhibits complement activation in a human body fluid; 2) inhibits the binding of purified human complement component C5 to either human complement component C3 or human complement component C4; and 3) does not specifically bind to the human complement activation product for C5a.

16. The method as in claim 12 wherein the antibody is administered as a first dose prior to performing the percutaneous transluminal coronary angioplasty; and a second dose of the antibody is subsequently administered by intravenously infusing the subject over a period of at least 4 hours.

17. The method as in claim 16 wherein the second dose is administered no later than 4 hours after the first dose.

18. The method as in claim 16 wherein the second dose is administered over a period of 8 to 24 hours.

19. The method as in claim 16 wherein the second dose is administered over a period of 12 to 20 hours.

20. A method of treating acute myocardial infarction comprising:
    administering a stent in connection with percutaneous transluminal coronary angioplasty, the stent comprising a coating that contains an anti-C5 antibody.

21. The method as in claim 20 wherein the antibody is h5G1.1-scFv.

22. The method as in claim 20 wherein the antibody is an antibody that directly or indirectly reduces the conversion of complement component C5 into complement components C5a and C5b.

23. The method as in claim 22 wherein the antibody comprising at least one antibody-antigen binding site, said antibody exhibiting specific binding to human complement component C5, said specific binding being targeted to the alpha chain of human complement component C5, wherein the antibody 1) inhibits complement activation in a human body fluid; 2) inhibits the binding of purified human complement component C5 to either human complement component C3 or human complement component C4; and 3) does not specifically bind to the human complement activation product for C5a.

* * * * *

UNITED STATES PATENT AND TRADEMARK OFFICE
CERTIFICATE OF CORRECTION

PATENT NO. : 7,361,339 B2 Page 1 of 1
APPLICATION NO. : 10/339562
DATED : April 22, 2008
INVENTOR(S) : Leonard Bell It is certified that error appears in the above-identified patent and that said Letters Patent is hereby corrected as shown below:

In the Title Item [54] please change "Morality" to correctly read -- Mortality --.

In the Claims:

In Claim 14, Col. 12, line 29, after "antibody" insert -- is --.

In Claim 23, Col. 13, line 1, after "antibody" insert --is an antibody--.

Signed and Sealed this

Second Day of September, 2008

JON W. DUDAS
*Director of the United States Patent and Trademark Office*

UNITED STATES PATENT AND TRADEMARK OFFICE
CERTIFICATE OF CORRECTION

PATENT NO. : 7,361,339 B2 Page 1 of 1
APPLICATION NO. : 10/339562
DATED : April 22, 2008
INVENTOR(S) : Leonard Bell It is certified that error appears in the above-identified patent and that said Letters Patent is hereby corrected as shown below:

In the Title Item [54] and Column 1, line 1, please change "Morality" to correctly read -- Mortality --.

In the Claims:

In Claim 14, Col. 12, line 29, after "antibody" insert -- is --.

In Claim 23, Col. 13, line 1, after "antibody" insert --is an antibody--.

This certificate supersedes the Certificate of Correction issued September 2, 2008.

Signed and Sealed this

Thirtieth Day of September, 2008

JON W. DUDAS
*Director of the United States Patent and Trademark Office*